United States Patent [19]

Wirt et al.

[11] Patent Number: 5,042,055

[45] Date of Patent: Aug. 20, 1991

[54] X-RAY THREADED PIPE JOINT ANALYSIS SYSTEM

[76] Inventors: Art Wirt, Rte. One, Box 333, Lafayette, La. 70508; Pierre J. Akar, 12015 Whittington, Houston, Tex. 77077

[21] Appl. No.: 491,741

[22] Filed: Mar. 12, 1990

[51] Int. Cl.⁵ .................. G01N 23/02; H05G 1/64
[52] U.S. Cl. ............................ 378/59; 378/58; 378/62; 378/56; 378/99; 358/111
[58] Field of Search ............... 378/59, 58, 62, 55, 378/4, 56, 11, 15, 20, 21, 24, 25, 207, 208, 99, 14; 250/254, 255, 256, 253; 358/111

[56] References Cited

U.S. PATENT DOCUMENTS

| | | |
|---|---|---|
| 3,178,576 | 4/1965 | Arvanetakis . |
| 3,666,944 | 5/1972 | Baldinger . |
| 4,066,899 | 1/1978 | Gaspar et al. ........................ 378/180 |
| 4,078,180 | 3/1978 | Green .................................... 378/99 |
| 4,411,014 | 10/1983 | Berman ................................ 378/58 |
| 4,422,177 | 12/1983 | Mastronardi et al. .............. 378/208 |
| 4,425,505 | 1/1984 | Jones et al. .......................... 378/55 |
| 4,542,520 | 9/1985 | Nelson ................................. 378/58 |
| 4,549,306 | 10/1985 | Shideler et al. ..................... 378/56 |
| 4,644,574 | 2/1987 | Dahn .................................... 378/58 |
| 4,660,419 | 4/1987 | Derkacs et al. ..................... 73/622 |
| 4,680,470 | 7/1987 | Heald ................................... 378/58 |
| 4,694,479 | 9/1987 | Bacskai et al. ...................... 378/59 |
| 4,809,308 | 2/1989 | Adams et al. ....................... 378/99 |
| 4,852,136 | 7/1989 | Larsson et al. ..................... 378/58 |

FOREIGN PATENT DOCUMENTS 977468 11/1975 Canada ................................. 358/5.1

*Primary Examiner*—Edward P. Westin
*Assistant Examiner*—Don Wong
*Attorney, Agent, or Firm*—Pravel, Gambrell, Hewitt, Kimball & Krieger

[57] ABSTRACT

A unit for producing an X-ray beam tangential to a threaded joint is disclosed. The X-beam is received and compared against a master sample. If there are any differences beyond allowable tolerances a failure indication is given. The tests are performed after the joint is made up but before the pipe is placed in the well, limiting remake costs. The X-ray beam is placed tangentially by shifting or rotating the beam as needed or by having a wide beam, so that tangents are obtained at two or more locations on the circumference of the joint. The unit may also compare pipe before making up a joint.

14 Claims, 8 Drawing Sheets

X-RAY THREADED PIPE JOINT ANALYSIS SYSTEM

BACKGROUND OF THE INVENTION

1. Field of the Invention

The invention relates to systems which analyze threaded joints and more specifically, to systems which use X-rays to observe the joint after assembly.

2. Description of the Prior Art

As it has become necessary in the past few years to drill deeper wells to obtain oil, the need for high yield strength casing and production tubing and strong connections between the various segments of the casing and the production tubing has increased. Testing of the pipe tube body forming the casing and tubing is generally done at the mill site and at the point where the pipe tube is to be threaded. At the threading location, various tests are performed to ensure that the threads meet design parameters. Additionally, hydrostatic pressure testing to approximately 80% of the strength of the pipe is generally performed. After the pipe is lowered into the well bore, in some instances a pressure test is performed with the pipe in tension, thus simulating certain well conditions and allowing a level of confidence to be developed after the pipe is in place.

It was eventually determined that over 50% of the downhole pipe failures occurred in the area of the connection for one of several different reasons. Therefore, there was significant attention focused on developing new types of connections with different thread parameters to help resolve significant numbers of these problems. Various other systems were developed to help make sure that a joint was properly made up or completed. In one of these systems, a computer system counted the number of turns the pipe member was making while measuring the torque applied to help ensure that the joint was properly made up. Speed control systems were developed so that the proper speed of assembly was used to help make up the joints. An alternate method used applied a mixture of inert gas such as nitrogen and helium to the connection area under pressure after the pipe was inserted into the well bore.

While these various systems were improvements over the prior systems, they still do not necessarily determine whether a joint is properly made up. The various pipe dopes, which are used to lubricate the joint during assembly, may be a major source of the leak after a period of time. The dope may first initially hide or seal a gap so that the various pressure-based techniques do not uncover the problem, but a leak eventually occurs because of the continuous pressure exerted when the pipe is inserted downhole. The masking ability and time to failure depend on the dope particle size and density.

The various tests currently performed before joint make up do not insure proper joint make up, but only that the individual parameters may be correct. Other methods utilized, such as the computerized system for measuring the number of turns and torque applied, are only indirect measurements and require relatively complicated assembly steps which increase the time required for a given operation and therefore the expense of drilling and developing the well. While the pressure testing provides a method for determining whether the complete pipe string is acceptable, should a failure be determined when the pipe is downhole, the entire string must be pulled to the point of flaw, thus necessitating a large expenditure and the increased possibility that the remaining joints which would then have to be remade could then be improperly formed.

U.S. Pat. No. 4,542,520 discloses a system for determining alignment of the hemispheres forming an inner sphere without disturbing an outer sphere. An X-ray beam is passed tangentially through the area of the hemisphere juncture. The patent discloses that the alignment is extrapolated from the curvatures of the hemispheres outside the seam weld because the exact junction can not be viewed.

U.S. Pat. No. 4,694,479 discloses a weld inspection system. An X-ray image from each of two different X-ray sources is made of a single weld from different angles. The images of the test weld are compared with the standard images of a perfect weld by an image comparator, which in turn produces a signal related to the quality of the comparison. A special-purpose computer determines the three dimensional coordinates of any defects.

SUMMARY OF THE INVENTION

The system of the present invention provides a means for observing the actual joint as made up prior to insertion into the well to determine if the joint parameters are within acceptable limits. If the joint parameters are within acceptable limits, then an indication of a good joint is given, while if there are flaws in the joint, an unacceptable indication is given.

The system of the present invention uses an X-ray source which sends X-rays tangentially through the joint to be received by an X-ray receiver and camera unit. The X-rays are transmitted through gaps in the joint so that a clear profile or outline of the separated portions of the joint, the separated male and female portions, can be observed. This image is then provided from the camera to an image processing system connected to a computer system, which compares the image received of the actual joint under test with a standard master for that particular pipe size, joint type, and manufacturer.

The camera provides a video image to the image processor, which then converts this video image into a series of pixels, each pixel representing a given location on the image and having a value indicative of its grey level. The grey values for a given area are reviewed to develop a mean and a mean deviation, which values are then compared against the mean and mean deviation for similar areas in the master, so that the pipe under test is compared with the master. If the computer determines that the joint under test is within given tolerance limits of the master joint, then the joint is considered acceptable. If the joint is not within acceptable limits, then it is considered a failed or bad joint. The joint must successfully pass all of a series of individual tests, such as cross-threading, compressed seal and open seal, prior to being considered an acceptable or good joint. If a failure is made in any one of the various tests at a given location, then the joint is considered unacceptable.

The tests are preferably performed at two or three different locations around the circumference of the joint, so that cross-threading and other various joint defects can be more readily determined. The various tangents can be obtained by several different ways, the first wherein the X-ray beam is normal to the longitudinal axis of the pipe and tangent to the center of the joint at one edge of the pipe. This beam is shifted from the first point on the joint across the diameter of the joint to a second point, so that two tangents which are located 180° apart are processed. In a different embodiment, the X-ray beam has a sufficient fan out or spread, so that when the center of the X-ray beam is positioned on the center line of the pipe, two tangents of the joint are obtained, which are received by one image receiving unit and camera. In this way, no shifting mechanism is required and yet two tangents will be obtained. Though the tangents are less than 180° apart, for smaller diameter joints they are sufficiently opposed for testing purposes. A third alternative involves an X-ray source which is also tangent to the circumference of the center line of the joint at one location, with the X-ray beam being rotated, preferably to three different locations at 120° increments, so that a series of images is obtained. There are various embodiments of the actual configuration of the X-ray source and X-ray receiver unit for each of the three variations.

Therefore the system of the present invention allows direct observation of the actual joint as made up and prior to insertion into the well. The direct observation is a better indicator of joint acceptability and the ability to test the made up joint prior to entry into the well bore saves the expense of removing and reinstalling pipe already placed.

BRIEF DESCRIPTION OF THE FIGURES

A better understanding of the invention can be obtained when the following detailed description of exemplary embodiments is considered in conjunction with the following drawings, in which.

DETAILED DESCRIPTION OF THE PREFERRED EMBODIMENTS

Figure 1:
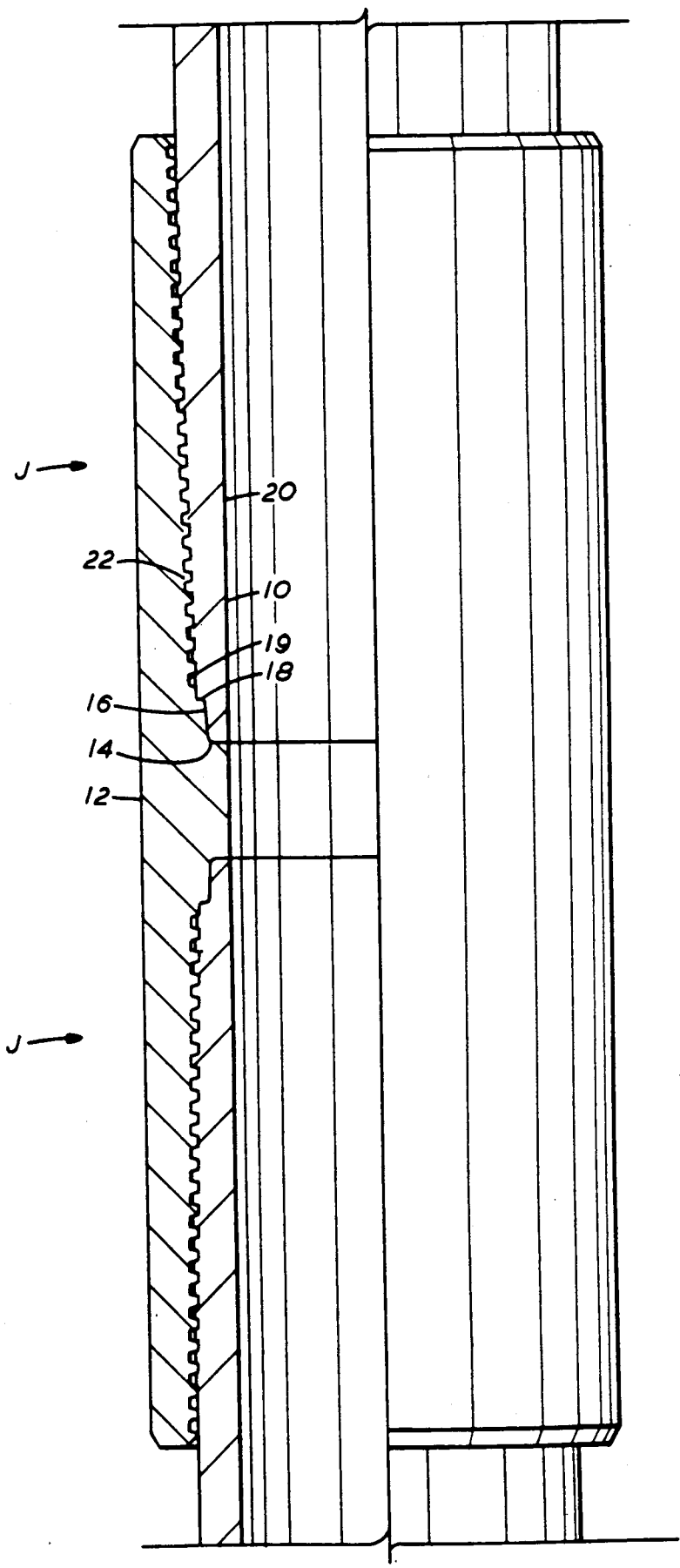
FIG. 1 is an illustration of properly made up joints comprised of two male sections of pipe with a female coupling unit.

Referring now to FIG. 1, two joints, each generally referred to by the letter J, are illustrated. The illustrated pipe connection is an example of properly made up joints comprised of two male sections of pipe 10 with a female coupling unit 12. In the illustrated embodiment, the joint J with one of the pipes includes a reserve shoulder 14, a radial seal 16, and a primary shoulder 18, proceeding from the end of the pipe 10 towards a threaded section 20. Just above the primary shoulder 18 in the coupling unit 12 is a portion of thread 22 with no mating portions of thread 22 on the pipe 10. The gap 19 thus formed is provided to allow the pipe dope or lubricant used in making up the joint J to have a location to reside to prevent the pipe dope from blocking full make up of the joint J. After a series of these unmated thread positions, mated threads commence and proceed for a given amount along the length of the pipe 10, according to the manufacturer's specifications. The exact characteristics of each thread, as well as of the various shoulders are based on the specifications of a given pipe size and joint type as developed by the pipe manufacturer. It is understood that the illustrated embodiments are for exemplary purposes only and are representative of the variations available. They are not intended to be limitations and those skilled in the art will be able to utilize the present invention with the array of joint specifications and configurations available.

As mentioned, the joints J shown in FIG. 1 are properly made up joints, where there are no gaps at the various seals or shoulders and the two sets of threads are properly mated, so that there is no cross-threading.

Figure 2:
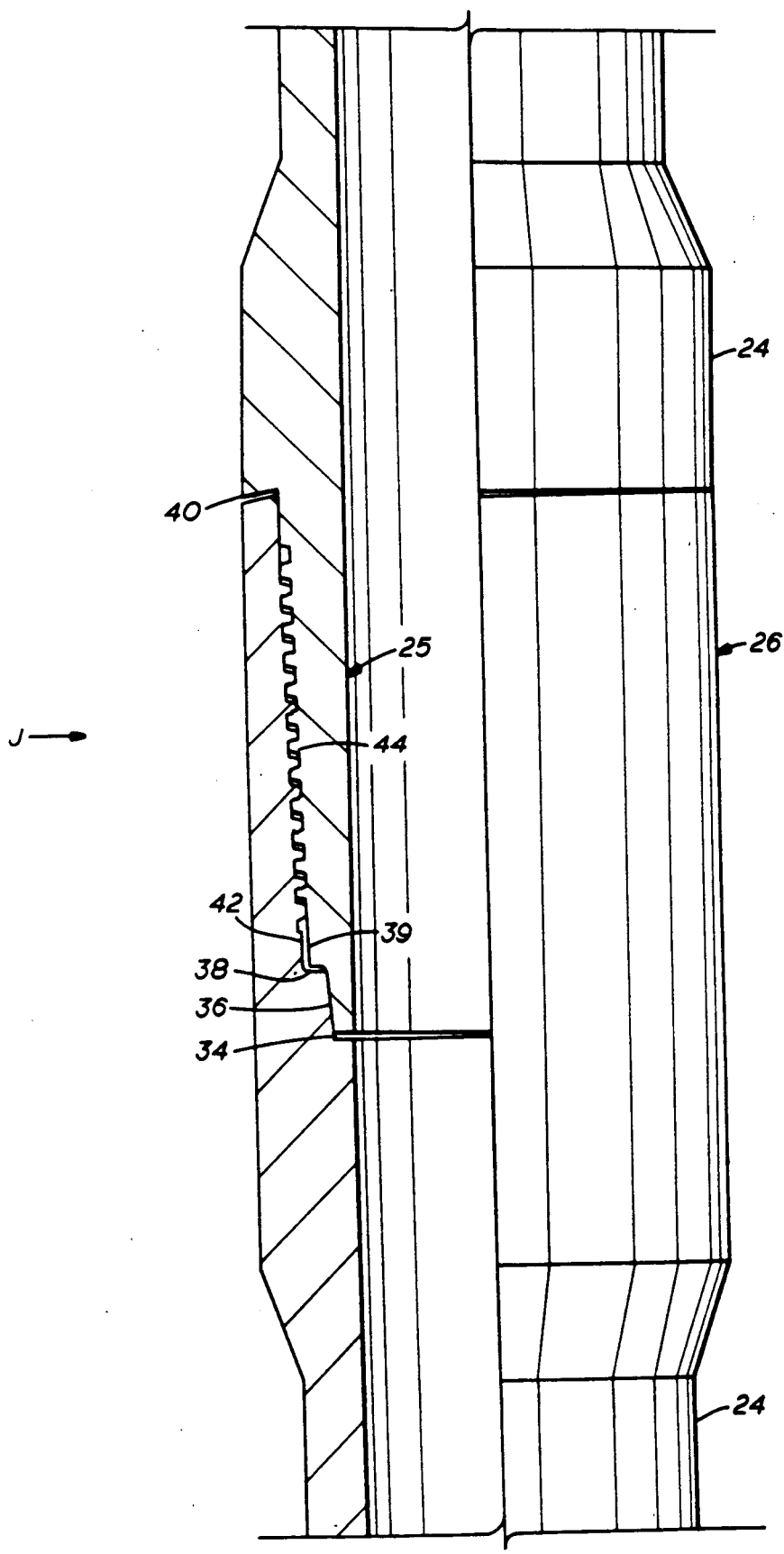
FIG. 2 is an integral joint made with pipe having one male and one female section with illustrations of bad seals and cross-threading.

FIG. 2 shows an integral type joint J wherein one section of pipe 24 contains the male portion 25 and the other end of a different section of pipe 24 contains a female portion 26. In the example shown, the joint J has a reserve shoulder 34, a radial seal 36, a primary shouler 38, and additionally has what is referred to as an external or inverse shoulder 40. In this joint J there is also a gap 39 adjacent the primary shoulder 38 to allow the pipe dope or lubricant to be positioned and not interfere with the joint make up. It must be noted in the example shown in FIG. 2 that the shoulders and threads are not properly mated between the male and female portions of the joint J. For example, in the particular joint made up in FIG. 2, the metal to metal radial seal is fully made but the various shoulders 34, 36 and 40 are not mated and the threads 44 of the two portions are not properly formed so that gaps have resulted in the primary and reserve shoulder portions, the inverse shoulder area and in the threads 44. Therefore, this clearly is not a properly made up joint and would undoubtedly fail in use.

Figure 3:
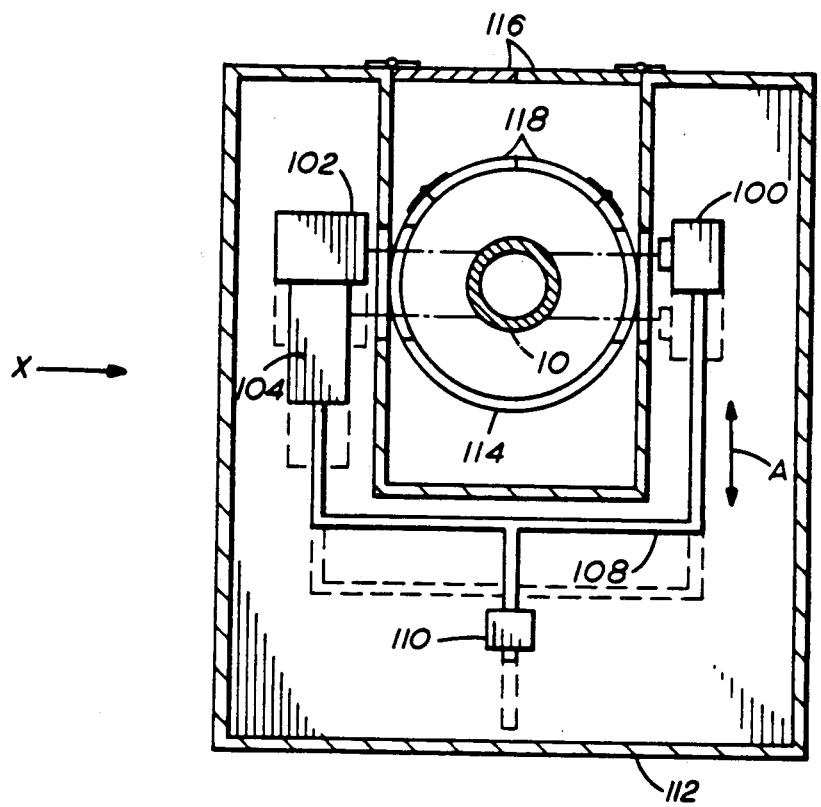
FIG. 3 is a partial cross-sectional top view of an assembly for transmitting and receiving X-ray signals in shifted mode according to the present invention.
Figure 9B:
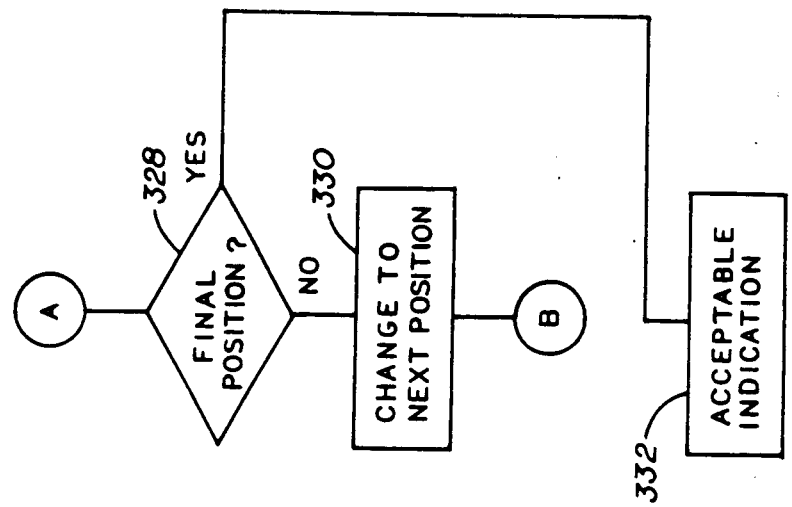
FIGS. 9A and 9B are flowchart illustrations of the operation of a system according to the present invention.
Figure 9A:
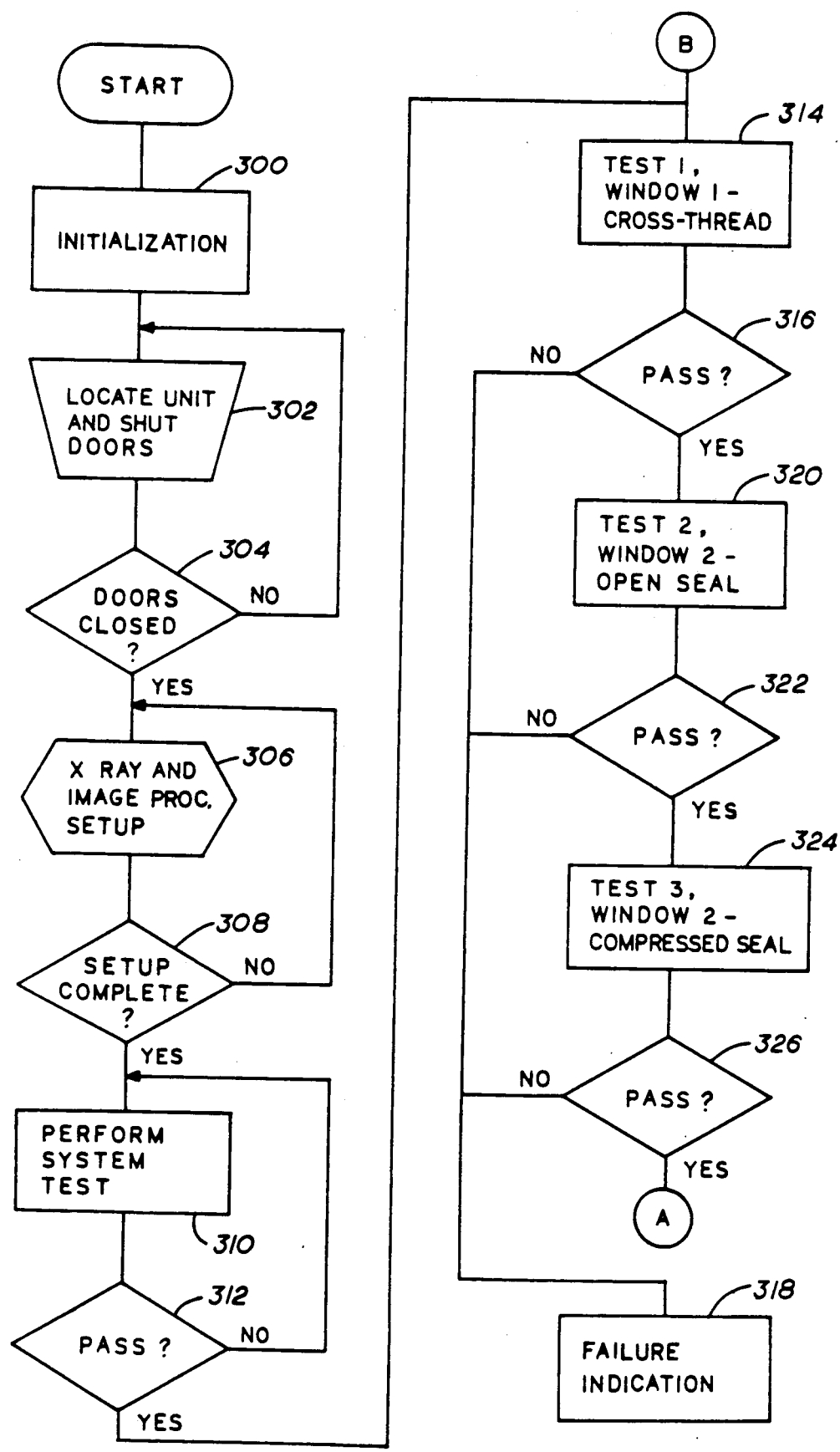

One embodiment of an X-ray detection unit X according to the present invention is shown in FIG. 3. The X-ray detection unit X includes an X-ray source 100 to produce an X-ray beam and an X-ray receiver 102 to receive the X-ray beam after it has passed through the pipe 10. The X-ray receiver 102 receives the X-ray beam and converts the X-rays to visible light. Connected to the X-ray receiver 102 is a camera 104 to convert the visible light image produced by the X-ray receiver 102 to an electrical signal for transmission to a computer system 106 (FIG. 9). The X-ray source 100, the X-ray receiver 102 and the camera 104 are all fixedly mounted to a movable frame 108, so that they are in a positive location to one another but can be moved in a direction laterally to the longitudinal axis of the pipe 10 as shown by the movement arrow A. This movement can be accomplished by means of an air cylinder 110 or other means which allows the frame 10 to move from a first position to a second position as shown in dashed lines in FIG. 3. The distance of the travel of the frame 108 is determined based on size of the pipe to be used on a specific job, so that when the frame 108 is in a first position, the X-ray receiver 102 receives the X-ray signal which has passed tangentially through the joint J in the pipe 10 and thus the received image includes an X-ray of the joint showing the threads and the various shoulders and seals. When the frame 108 is moved to its second position, the X-ray source 100 and X-ray receiver 102 are then at such a position that the X-ray beam which is received has traveled through a section of the joint J diametrically opposite of the previous location, so that two samplings of the joint J are made 180° apart, to allow cross-threading and other problems to be positively determined.

To protect the various components from damage in the harsh oil field environment, a housing 112 encloses the various moving assemblies and components. Additionally, to protect the operators from the X-ray beam, the pipe 10 is positioned inside a lead cylinder 114 so that any X-rays that are not traveling to the X-ray receiver 102 are absorbed by the lead and thus the amount of exposure to any worker located on the rig is reduced.

The pipe 10 must be located properly inside the U-shape formed by the X-ray source 100 and the X-ray receiver 102 and thus must be moved inside both the housing 112 and the lead cylinder 114. To this end, the housing 112 contains doors 116 which are opened to allow the pipe 10 to be moved into the housing 112. The lead cylinder 114 also contains doors 118 which are opened to allow the pipe 10 to be moved in the cylinder 114. Located and cooperating with the doors 118 and the doors 116 are electrical switch assemblies 204 (FIG. 8) to indicate whether the doors are opened or closed, so that the unit X can only be operated after all of the doors 116 and 118 are closed, to reduce the possibility of the accidental X-ray exposure.

Figure 4:
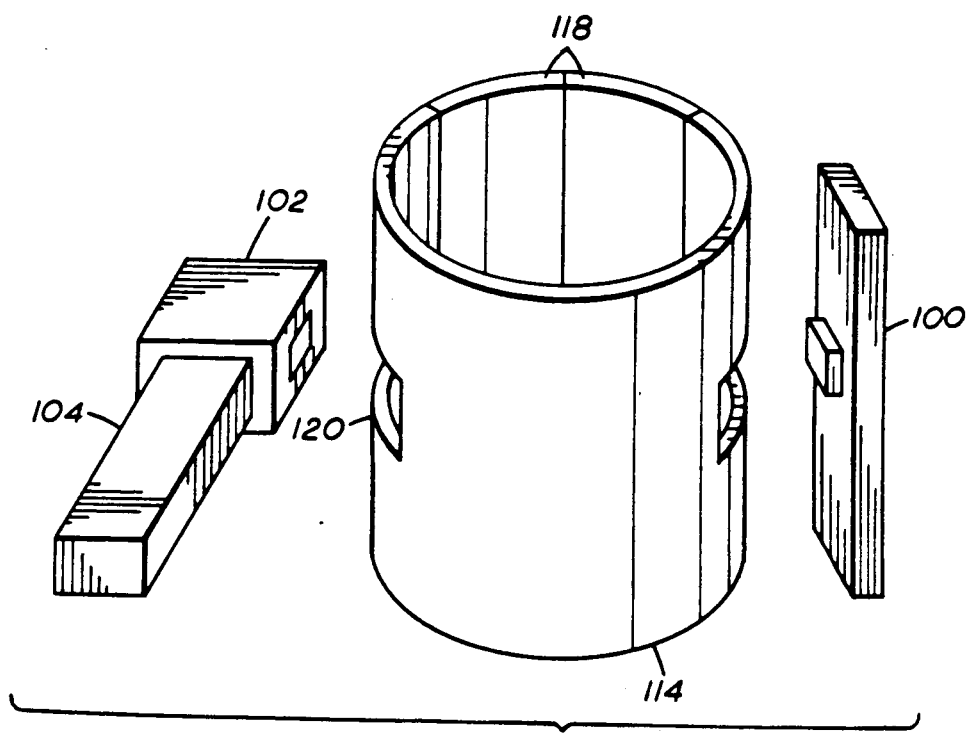
FIG. 4 is a perspective view of portions of the assembly of FIG. 3.

The lead cylinder 114 must, however, contain slots so that the X-ray beam generated by the X-ray source 100 can travel through the lead cylinder and not be blocked. The slots are shown as slots 120 (FIG. 4) and in the embodiment of FIG. 3 are such that their width allows the X-ray source 100 to be moved to both necessary positions for the given pipe size under test. The slots 120 can be of one width to cover all pipe sizes or the lead cylinder 114 can be replaceable by the manufacturer so that only the minimum size of the slots 120 necessary is utilized in a given installation.

Figure 5:
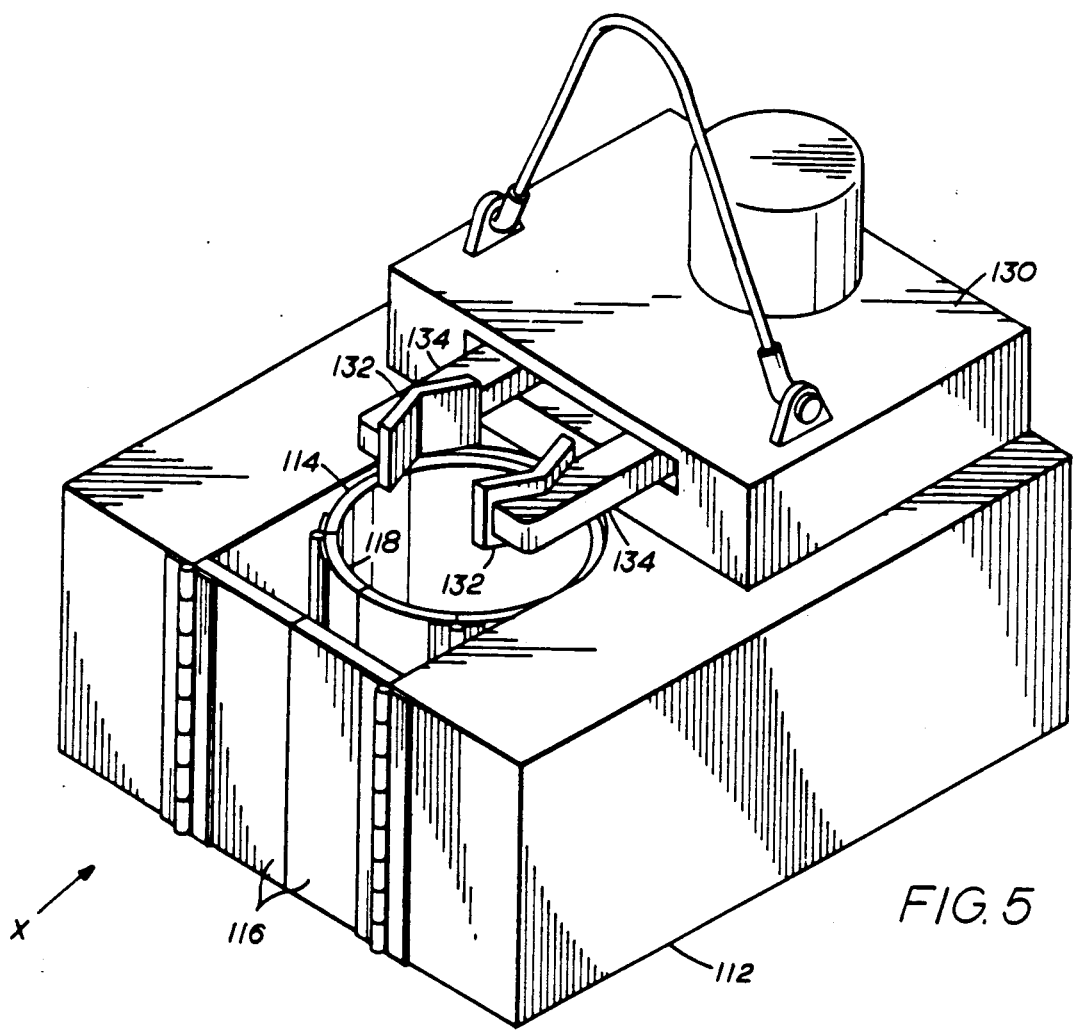
FIG. 5 is a perspective view of the outer housing of a system according to the present invention.

To be properly observed, the pipe 10 must be located preferably coaxially with the axis of the lead cylinder 114 but should at least be located in a given fixed location in relationship to the travel of the frame 108 and the X-ray source 100. To this end, a variation or simplified design of a tong 130, either manual or power, is located on top of the housing 112 to position the pipe 10 (FIG. 5). The tong 130 shown in FIG. 5 is a highly simplified drawing to illustrate the principal of operation in that two jaws 132 are located on opposing arms 134, which are closed around the pipe 10, with the pipe 10 located in such a position that the joint J is properly located vertically within the X-ray beam to be properly imaged. The jaws 132 correctly position the pipe axis with regard to the central axis of the lead cylinder 114 so that, based on the known size of the pipe 10 to be used for a given situation, the X-ray source 100 in its first position of the frame 108 is positioned correctly to provide a tangent through the joint, with the second location being based then upon the proper travel of the frame 108.

The pipe 10 is positioned for testing by opening the housing doors 116 and the lead cylinder doors 118, positioning the pipe 10 between the jaws 132 and closing the jaws 132 about the pipe 10 to fix it in place. The lead cylinder doors 118 are then closed and the housing doors 116 are closed, so that everything is positioned and the door switches 204 are set to allow operation.

Figure 6:
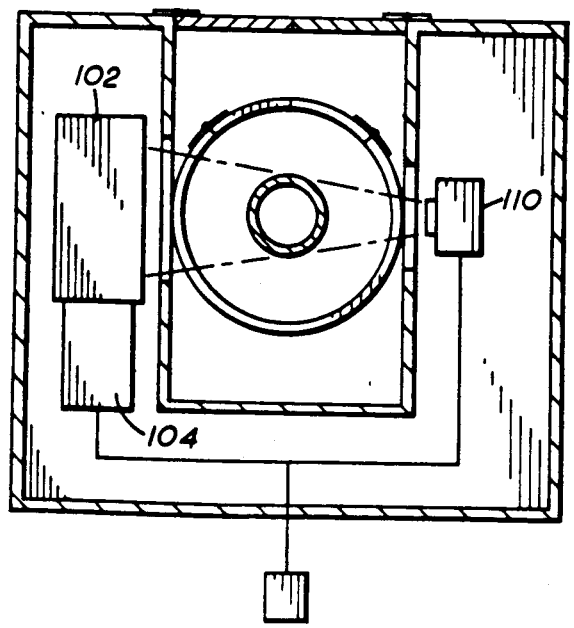
FIG. 6 is an alternate embodiment showing an embodiment having an X-ray beam which is tangent to two locations from one X-ray source location.

In an alternate embodiment (FIG. 6), the X-ray source 100 and the X-ray receiver 102 need not be located on a movable frame 108. In this embodiment the X-ray source 100 emits an X-ray beam which has sufficient fan-out or beam spread so that the beam traverses two tangents on the pipe 10 which are then received by the X-ray receiver 102. It is noted that the X-ray receiver 102 could have one large active area or it could have two small active areas properly located to receive just the tangential X-ray beams. The separation between the two individual active areas would be properly aligned at the factory prior to use based on the given pipe size to be used at that well site. Thus in this embodiment, there is no need to attach the various items to a movable frame 108 and the complexity of the unit X is simplified.

Figure 7:
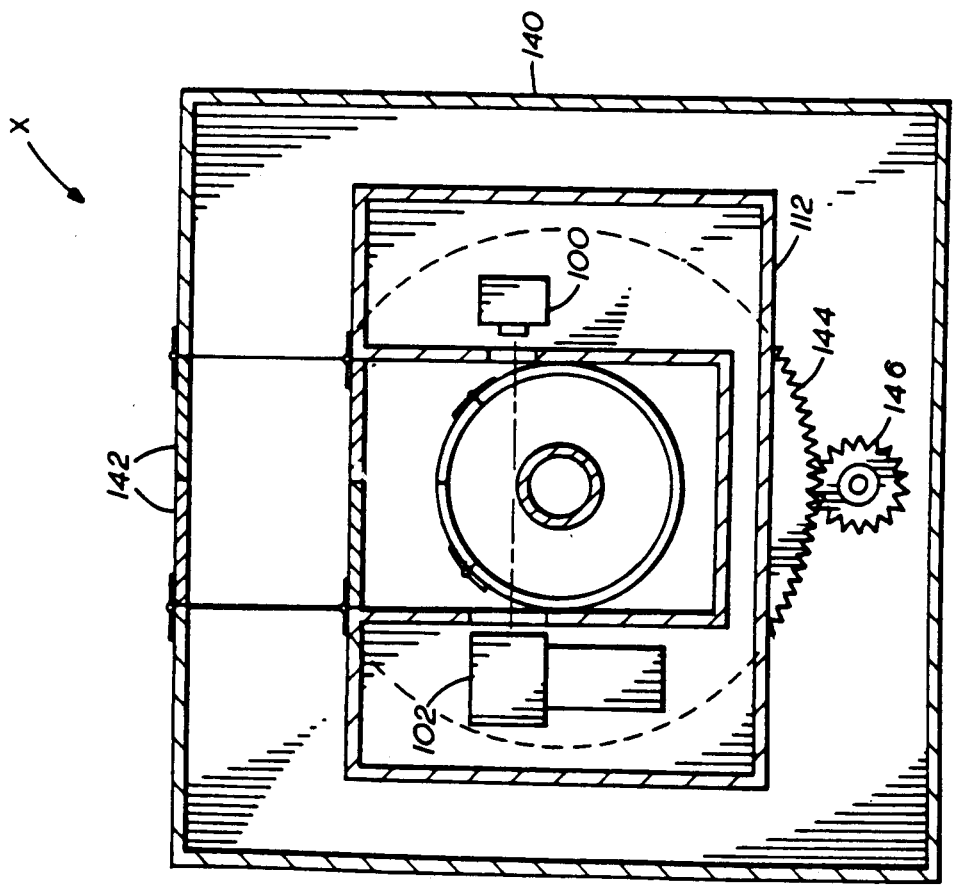
FIG. 7 is a partial cross-sectional view of a system for determining multiple tangents by rotating the unit around the pipe, with the unit being in the 0° position.

In yet another alternate embodiment (FIG. 7), the X-ray source 100 and the X-ray receiver 102 are fixedly mounted to the housing 112 in a position such that the X-ray beam is tangent to the pipe 10 at one location. In this case, the housing 112 is located inside yet a larger outer protective housing 140, which has its own set of doors 142 with additional interlock switches 204. In this example, the housing 112 with its attached X-ray source 100 and X-ray receiver 102 is rotated about the pipe 10 so that preferably three different locations are X-rayed for analysis. One example and manner of rotating the housing 112 is to place a ring gear 144 or similar device on the bottom of the housing 112 with a motor driven pinion gear 146 attached fixedly to the outer housing 140. Thus, as the motor turns the pinion gear 146, the ring gear 144 attached to the housing 112 rotates.

In operation, the pipe 10 is located with the housing 112 positioned as illustrated, with the U-shape of the housing 112 aligned with the U-shape of the outer housing 140. The housing 112 is then rotated to the desired positions, preferably three 120° tangents, so that three samples are taken for a more thorough analysis.

Figure 8:
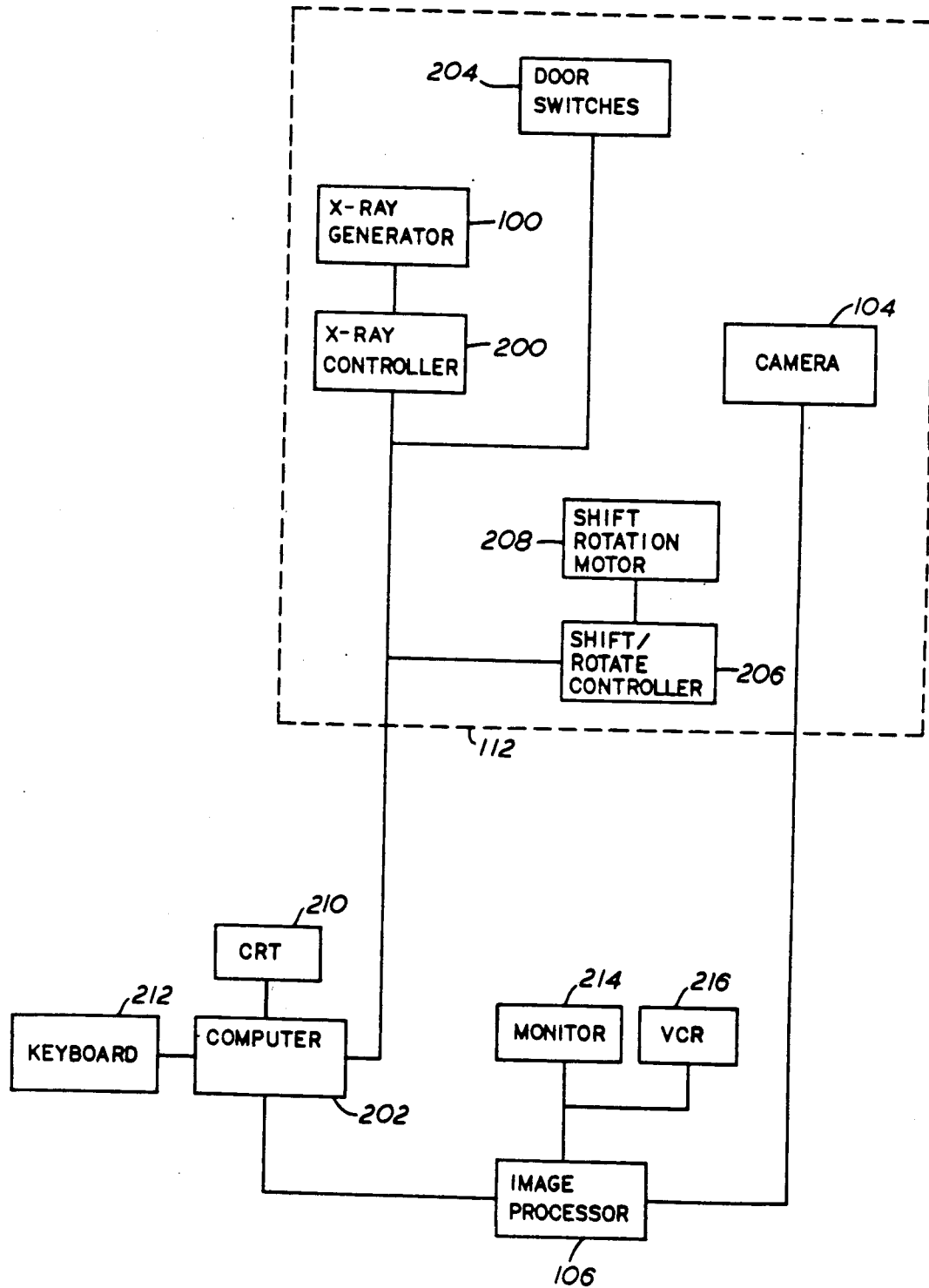
FIG. 8 is an electrical schematic block diagram of a system according to the present invention.

Various portions of the circuitry and electronics necessary to perform the joint analysis are located in the housing 112. For example, the X-ray source or generator 100 is connected to an X-ray controller 200 (FIG. 8). This X-ray controller 200 is then connected to a computer 202 which is running appropriate software to control the device. Also connected to the computer 202 are the various door switches 204 and rotation position sensors 206 used to determine whether the various doors 116, 118 and 142 are closed and if the inner housing 112 rotation should be stopped. The doors switches 204 provide the necessary feedback to the computer 202 to provide the interlock utilized in the control of the X-ray generator 100 to reduce the possibility that the operators and workers nearby are not irradiated accidentally. Also connected to the computer 202 and located within the housing 112 is a shift or rotation controller 206. This controller 206 is utilized to interface the computer 202 to the air solenoid 110 in the case of the shifting assembly of FIG. 3 or to the rotation motor 208 of the embodiment of FIG. 8. A CRT display 210 and a keyboard 212 are connected to the computer 202 and used by the operator to control operations and interact with the computer 202 as necessary.

The camera 104, which is located inside the housing 112, is connected to an image processor 106 which receives and digitizes the received image of the X-ray beam made visible by the X-ray receiver 102. The image processor 106 has connected to it a monitor 214 so that the X-ray image can be reviewed in real time by the operator and a video cassette recorder 216 so that any received images can be recording for record-keeping purposes. The image processor 106 is connected to the computer 202, preferably by being a circuit board unit which is located inside the computer itself to allow very high speed communications. Alternately, the image processor 106 can be a stand alone unit which is connected via various communications interfaces to the computer 202. Thus the computer 202 receives digitized information from the image processor 106 and analyzes the digitized information as necessary. Alternatively, sufficient computational power and devices can be present on the image processor 106 so that the computer 202 need only send over certain commands and have defined operations performed by the image processor 106.

To properly operate, the computer 202 must have operating instructions. These operating instructions are illustrated in a flowchart form in FIGS. 9A and 9B. The operation sequence starts at step 300 where the initialization of necessary variables and parameters is performed. In step 302, it is indicated to the operator that the pipe 10 should be located in the unit X, generally by moving the unit X to the pipe 10 which is in position on the drilling rig, the tongs 130 should be closed, and the various doors 116, 118 and 142 should be shut. In step 304, the computer 202 determines whether the doors 116, 118 and 142 have been properly closed by interrogating the state of the door switches 204. If the doors 116, 118 and 142 are not closed, control returns to step 302 and the locate unit and shut doors message is repeated to the operator. If the doors are properly closed, indicating that the pipe 10 and the unit X are positioned, control proceeds to step 306 where setup instructions are transmitted to the X-ray controller 200 and to the image processor 106 to allow them to be prepared to operate.

In step 308, the computer 202 then evaluates whether the setup is complete as received by monitoring feedback information from the X-ray controller 200 and the image processor 106. If the setup is not complete for some reason, step 308 transfers control to step 306 where setup is again requested. If the setup is completed, control proceeds to step 310 where a system test is performed. This is done to calibrate the unit X if necessary and to put the unit X in a final readiness state for operation. If the computer 202 determines in the next step, step 312, that the unit X did not pass the system test, control returns to step 310 and the system test is repeated. If, however, the unit X does pass the system test, control proceeds from step 312 to step 314, where the first test is performed.

Figure 10A:
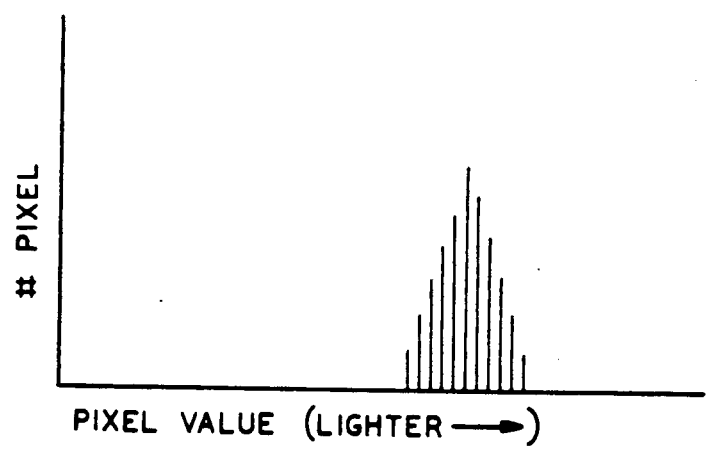
FIGS. 10A, 10B and 10C are graphs illustrating various analysis cell histograms.
Figure 10B:
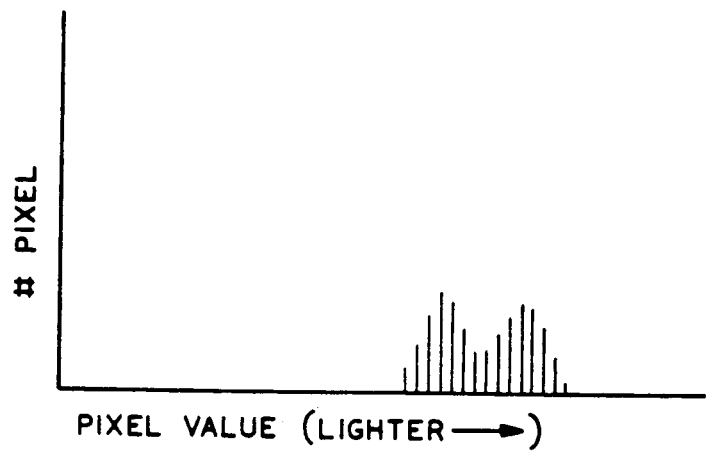
Figure 10C:
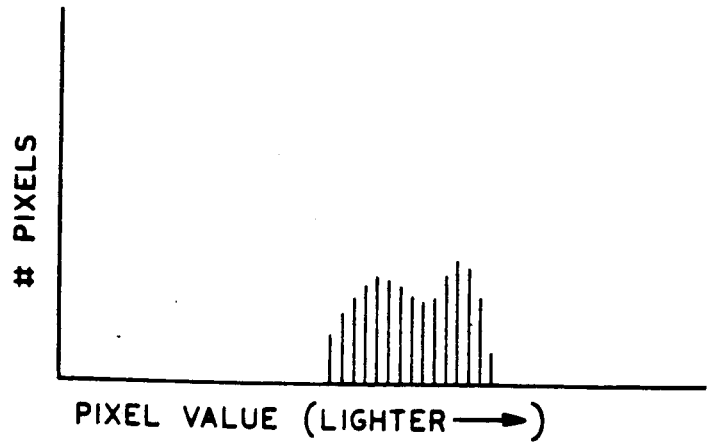

A test consists primarily of a histogram based analysis of the necessary area of the sampled image. The camera 104 produces an image which is a series of scan lines. In the preferred embodiment, approximately 480 lines are developed for each image. The image processor 106 converts the received image from the camera 104 to a series of digital values by sampling each scan line a number of times, in the preferred embodiment 640. Each sample represents a dot or pixel of the image and has darkness or grey level associated with it. A high value grey level is considered whiter, while a lower value is darker. With these digitized pixel values, the computer 202 selects a given area of pixels, for example, a 50 x 50 cell, and performs a histogram analysis on the cell. In this analysis, the number of pixels at a given grey scale level are evaluated. The mean and mean deviations of the various pixel values for the cell are determined. For example, in an ordinary metal location or in a good seal, the pixel values may generally end up as a bell-shaped curve as shown in FIG. 10A. If, for example, a seal is not made up properly and there is a gap, then the pixel values will have a shift toward the lighter end (FIG. 10B) because more X-rays will pass through the gap and thus the image presented by the X-ray receiver 102 will be brighter. Thus, in this case, the mean and mean deviations will be different from those of a properly made up joint. Alternately, if there is supposed to be a gap at a given location and the image is darker, as shown in FIG. 10C, because of the presence of metal, for example, a cross-threaded area or an area where the metal has been deformed and bulged out into a normally vacant area, the mean and mean deviation will have a tendency to move toward the darker end of the pixel valve scale values and thus also be different.

A test is performed by comparing the histogram mean and mean deviation values of the cells of the sample under test with the appropriate and equivalent histogram values for a master sample of a properly made up joint which is stored in the computer 202. A library of master samples can be developed and the appropriate master sample data can be included with a unit X on a particular job. The master sample joint would be X-rayed using the same unit X and could be destructively tested to determine its quality. Thus the computer is testing the made up joint which is to be inserted into the well against a master reference. The test will, of course, have certain allowable tolerances based on the actual specifications of the joint as developed by the joint manufacturer. These tolerances will be acknowledged in the test and used in the pass or fail criterion.

In step 314 the first test is performed, where an evaluation is made to determine whether the joint J has cross-threaded. An X-ray image is received, the image is registered with the master sample to align the two images and the histogram analysis is performed. In this case the test is made at the first location, the flowcharts being developed for the shifting unit X of FIG. 3. If, after the computer 202 has determined the various histogram values for all of the various cells and they are not within given ranges as compared against the master, thus indicating an unacceptable joint J, control passes from step 316 to step 318 where a failure indication is given to the operator. This means that the operator must take the joint apart and reform the joint. This has occurred prior to entry of the entire pipe downhole and thus it is easier to reform the joint at this time than to pull portions of the pipe that are in the ground and replace the pipe or remake the joint.

If this first test was successful, control passes from step 316 to step 320 where a second test is performed. In test 2, the sample is tested to see whether there are open seals at the various seal and shoulder locations. Again this test is performed using the standard registration and histogram techniques as previously discussed. If the joint under test does not pass, step 320 transfers control to step 318 where a failure is indicated. If the test is passed, step 322 transfers control to step 324 where a third test, the compressed seal test, is performed. If the compressed seal test is also passed for this particular location on the joint, then control proceeds from step 326 where a final position determination is made in step 328. However, if this location in the joint did not pass the test, then step 326 transfers control to step 318 and failure is indicated.

After the third test has been completed and passed, step 328 then determines whether the X-ray unit 100 and X-ray receiver 102 are in the final position. If not, control proceeds to step 330 where the appropriate signals are developed by the computer 202 to cause the assembly to shift or rotate as necessary. Control then proceeds to step 314 where the three tests are then commenced at this second location.

If, in step 328, it was determined that this was the final position and that therefore all three tests had been performed at all necessary locations, then control proceeds to step 332 where an acceptable indication is given and the pipe 10 can be inserted into the well bore.

As can be seen, this is a fully automatic operation once the joint is properly positioned, thus allowing a high repeatability of operation at a relatively low cost. It should also be noted that the analysis operation to determine joint acceptability is performed prior to the joint entering the hole but after the specific joint that is to be placed into the well is made up. Thus, each joint which is actually to be installed is tested and if it is unacceptable the entire pipe string does not have to be removed from the well for replacement of the particular bad sections.

While the above discussion has focused on using the unit X to evaluate joints, it is to be noted that the unit X can also be used with pipe 10 which has not been made up to inspect the various thread parameters. The pipe would be positioned as discussed and the unit X would operate as discussed, but the master sample would be for a similar pipe not made up into a joint. Thus, one unit can perform the standard thread parameter check and the joint inspection, reducing the need for duplicate inspection equipment.

The foregoing disclosure and description of the invention are illustrative and explanatory thereof, and various changes in the size, shape, materials, components, circuit elements, wiring connections and contacts, as well as in the details of the illustrated circuitry and construction and method of operation may be made without departing from the spirit of the invention.

We claim:

1. An apparatus for determining threaded pipe joint acceptability of a pipe fixed in a given location, comprising:
   means for producing an x-ray beam projecting tangentially through at least two different locations on the circumference of the threaded pipe joint;
   means for receiving the x-ray beam at each tangent of the threaded pipe joint and producing an electrical signal representative of an image of the received x-ray beam;
   means for comparing said electrical signal with a stored acceptable joint image to determine if the received image is within satisfactory tolerance limits of the acceptable image;
   means for producing an acceptance indication if the joint is acceptable; and
   means for producing a failure indication if the joint is unacceptable.

2. The apparatus of claim 1,
   wherein said X-ray beam producing means includes means for producing an X-ray beam projecting tangentially to only one tangent location of the threaded pipe joint at a given time and means for moving said one tangent X-ray beam producing means to a different tangent location of the threaded pipe joint, and
   wherein said X-ray beam receiving means moves with said one tangent X-ray beam producing means to receive the X-ray beam.

3. The apparatus of claim 2, wherein
   said means for moving said one tangent X-ray beam producing means moves said beam normally with respect to a longitudinal axis of the pipe.

4. The apparatus of claim 2, wherein said means for moving said one tangent X-ray beam producing means rotates around a longitudinal axis of the threaded pipe joint.

5. The apparatus of claim 1, wherein said X-ray beam producing means includes means for producing an X-ray beam having a dispersion angle sufficient to be tangential to the threaded pipe joint at two locations.

6. The apparatus of claim 1, wherein said X-ray beam receiving means includes an X-ray receiver and a camera having an electrical signal output.

7. The apparatus of claim 1, wherein said image comparing means includes:
   means for digitizing said electrical signal;
   means for comparing said digitized signal against a digitized acceptable image; and
   means for determining if the compared signal and image are within given tolerance limits.

8. An apparatus for determining threaded pipe portion acceptability of a pipe fixed in a given location, comprising:
   means for producing an x-ray beam projecting tangentially through at least two different locations on the circumference of the threaded portion of a pipe;
   means for receiving the x-ray beam at each tangent of the pipe and producing an electrical signal representative of an image of the received x-ray beam;
   means for comparing said electrical signal image with a stored acceptable pipe image to determine if said electrical signal is within satisfactory tolerance limits of the acceptable image;
   means for producing an acceptance indication if the threaded portion is acceptable; and
   means for producing a failure indication of the threaded portion is unacceptable.

9. A method for determining threaded pipe joint acceptability of a pipe fixed in a given location, comprising:
   producing an x-ram beam projecting tangentially through at least two different locations on the circumference of the threaded pipe joint;
   receiving the x-ray beam at each tangent of the threaded pipe joint and producing an electrical signal representative of an image of the received x-ray beam;
   comparing said electrical signal with a stored acceptable joint image to determine if said electrical signal is within satisfactory tolerance limits of the acceptable image;
   producing an acceptance indication if the joint is acceptable; and
   producing a failure indication if the joint is unacceptable.

10. The method of claim 9,
    wherein said X-ray beam producing step includes producing an X-ray beam projecting tangentially to only one tangent location of the threaded pipe joint at a given time and moving said one tangent X-ray beam to a different tangent location of the threaded pipe joint.

11. The method of claim 10, wherein
said step of moving said one tangent X-ray beam moves said beam normally with respect to a longitudinal axis of the pipe.

12. The method of claim 10, wherein said step of moving said one tangent X-ray beam rotates said beam around a longitudinal axis of the threaded pipe joint.

13. The method of claim 10, wherein said X-ray beam producing step includes producing an X-ray beam having a dispersion angle sufficient to be tangential to the threaded pipe joint at two locations.

14. The method of claim 10, wherein said image comparing step includes:
digitizing said electrical signal;
comparing said digitized signal against a digitized acceptable image; and
determining if the compared signal and image are within given tolerance limits.

* * * * *